United States Patent
Makris et al.

(10) Patent No.: US 11,694,805 B1
(45) Date of Patent: Jul. 4, 2023

(54) USING MACHINE LEARNING TO PREDICT PATIENT RISK ASSOCIATED WITH RESPIRATORY CONDITIONS

(71) Applicant: WALGREEN CO., Deerfield, IL (US)

(72) Inventors: Evie Makris, Deerfield, IL (US); Tanya Grace Singh, Mundelein, IL (US); Renae Lin Smith-Ray, Riverside, IL (US); Alexandra Broadus, Deerfield, IL (US)

(73) Assignee: WALGREEN CO., Deerfield, IL (US)

(*) Notice: Subject to any disclaimer, the term of this patent is extended or adjusted under 35 U.S.C. 154(b) by 213 days.

(21) Appl. No.: 16/917,380

(22) Filed: Jun. 30, 2020

(51) Int. Cl.
| | |
|---|---|
| *G16H 50/20* | (2018.01) |
| *G16H 50/30* | (2018.01) |
| *G16H 20/10* | (2018.01) |
| *G16H 50/70* | (2018.01) |
| *G16H 70/40* | (2018.01) |
| *G16H 10/20* | (2018.01) |
| *G16H 10/60* | (2018.01) |
| *A61B 5/00* | (2006.01) |

(52) U.S. Cl.
CPC .......... *G16H 50/20* (2018.01); *A61B 5/0022* (2013.01); *A61B 5/4833* (2013.01); *A61B 5/7267* (2013.01); *A61B 5/7275* (2013.01); *G16H 10/20* (2018.01); *G16H 10/60* (2018.01); *G16H 20/10* (2018.01); *G16H 50/30* (2018.01); *G16H 50/70* (2018.01); *G16H 70/40* (2018.01)

(58) Field of Classification Search
CPC ........ G16H 50/20; G16H 10/60; G16H 50/30; G16H 50/70; G16H 70/40; G16H 20/10; A61B 5/0022; A61B 5/4833; A61B 5/7267; A61B 5/7275
USPC .............................................................. 705/2
See application file for complete search history.

(56) References Cited

U.S. PATENT DOCUMENTS

| | | | | |
|---|---|---|---|---|
| 2017/0286622 | A1* | 10/2017 | Cox | G16Z 99/00 |
| 2021/0158925 | A1* | 5/2021 | Hanina | A61B 5/4833 |
| 2022/0277841 | A1* | 9/2022 | Harmon | G16H 10/60 |
| 2023/0038292 | A1* | 2/2023 | Barrett | G16H 10/60 |

* cited by examiner

*Primary Examiner* — Michael Tomaszewski
*Assistant Examiner* — Rachael Sojin Stone
(74) *Attorney, Agent, or Firm* — Marshall, Gerstein & Borun LLP; Randall G. Rueth

(57) ABSTRACT

Systems and methods for using machine learning models to predict risks posed to patients having various respiratory conditions. According to certain aspects, an electronic device may generate a machine learning model using training data indicating various patient and medication data. The electronic device may access a set of real-world patient data and input the real-world patient data into the machine learning model. An output of the machine learning model may indicate a likelihood of the patients needing intervention care, and the electronic device may facilitate outreach efforts to certain patients in an attempt to decrease this likelihood.

16 Claims, 5 Drawing Sheets

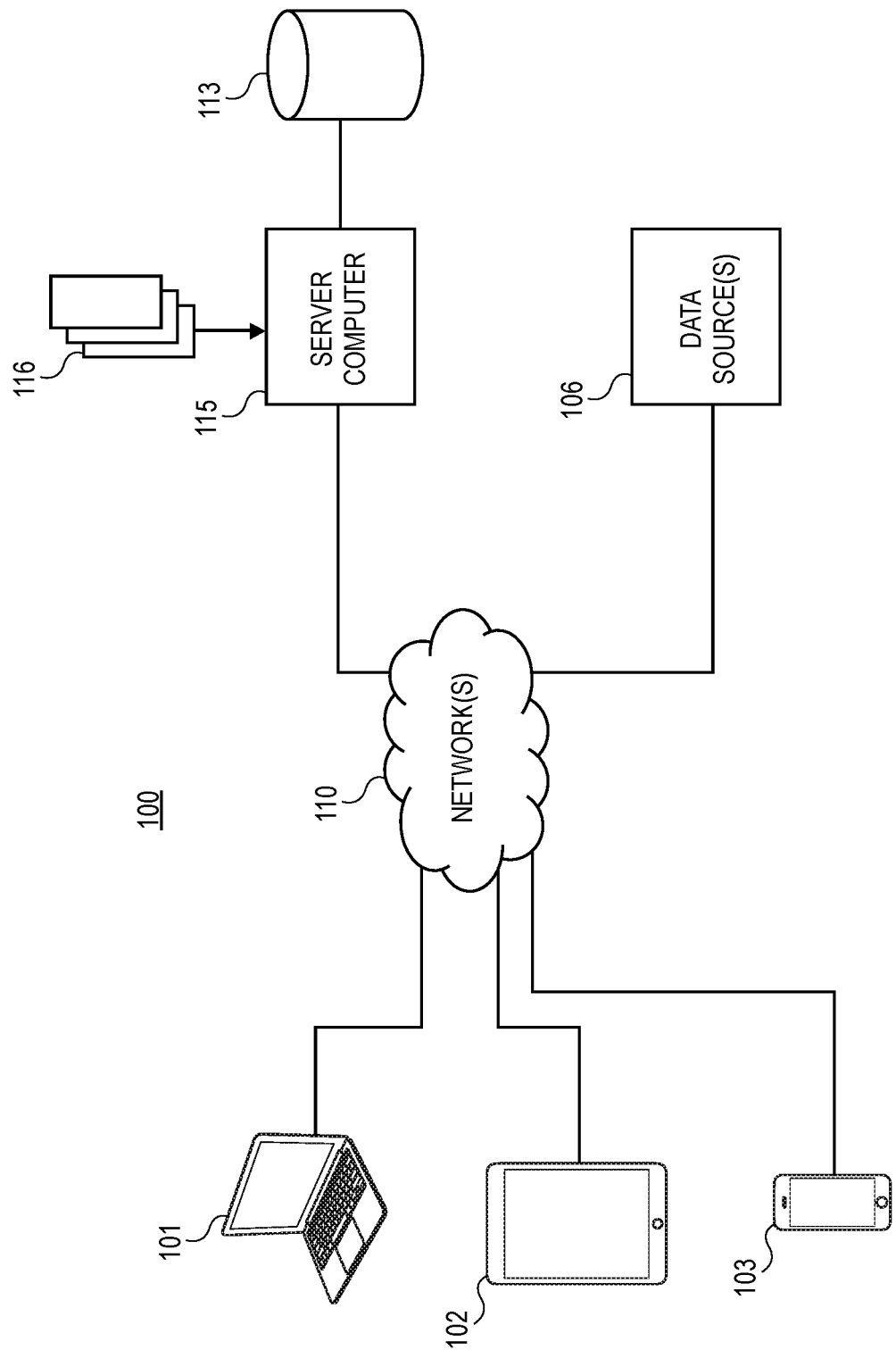

USING MACHINE LEARNING TO PREDICT PATIENT RISK ASSOCIATED WITH RESPIRATORY CONDITIONS

FIELD

The present disclosure is directed to using machine learning to predict patient risks. More particularly, the present disclosure is directed to platforms and technologies for using machine learning to predict likelihoods of patients needing additional care or treatment in association with respiratory conditions.

BACKGROUND

Respiratory health is of significant importance and concern for individuals and communities, as people can suffer from various respiratory conditions such as asthma, bronchitis, and chronic obstructive pulmonary disease (COPD), which includes emphysema. For example, more than twenty five (25) million people in the United States have asthma, including six million children. Further, more than sixteen (16) million Americans have been diagnosed with COPD and 140,000 deaths are attributed to COPD each year. The burden of these conditions affects individuals, families, schools, workplaces, and society itself, as in addition to the health concerns for individuals, treating such conditions is taxing on healthcare systems.

Respiratory conditions are often treated with prescription medications. For example, asthma may be treated with some combination of inhaled corticosteroids, long-acting beta2-agonists, rescue inhalers, and other medications. However, patients may not always adhere to their medication regimens, which increases the risk of these patients needing additional care, such as an emergency room or urgent care visit, or hospitalization. Although certain medical personnel may have access to adherence information for patients, it is still difficult or impossible for the medical personnel to accurately and effectively predict the likelihood of certain patients needing additional care.

Accordingly, there is an opportunity to employ machine learning systems and techniques to accurately predict risks posed to certain patients according to various patient attributes, adherence levels, and other factors.

SUMMARY

In an embodiment, a computer-implemented method for predicting patient risk is provided. The method may include: generating, by a processor, a machine learning model using an initial dataset identifying a plurality of patients, the initial dataset comprising prescription information indicating a plurality of adherence levels respectively by the plurality of patients to a plurality of medications prescribed in association with a respiratory condition; accessing, by the processor, an additional dataset identifying an additional plurality of patients, the additional dataset comprising prescription information indicating an additional plurality of adherence levels respectively by the additional plurality of patients to an additional plurality of medications prescribed in association with the respiratory condition; inputting, by the processor, the additional dataset into the machine learning model; and after inputting the additional dataset into the machine learning model, outputting, by the processor, a result from the machine learning model, the result comprising a set of risk levels respectively associated with at least a portion of the additional plurality of patients.

In another embodiment, a system for predicting patient risk is provided. The system may include a processor, a memory storing data associated with a machine learning model, and a non-transitory computer-readable memory interfaced with the processor and the memory, and storing instructions. The instructions, when executed by the processor, may cause the processor to: generate the machine learning model using an initial dataset identifying a plurality of patients, the initial dataset comprising prescription information indicating a plurality of adherence levels respectively by the plurality of patients to a plurality of medications prescribed in association with a respiratory condition, access an additional dataset identifying an additional plurality of patients, the additional dataset comprising prescription information indicating an additional plurality of adherence levels respectively by the additional plurality of patients to an additional plurality of medications prescribed in association with the respiratory condition, input the additional dataset into the machine learning model, and after inputting the additional dataset into the machine learning model, output a result from the machine learning model, the result comprising a set of risk levels respectively associated with at least a portion of the additional plurality of patients.

In a further embodiment, a non-transitory computer-readable storage medium having stored thereon a set of instructions, executable by a processor, for predicting patient risk is provided. The instructions may include: instructions for generating a machine learning model using an initial dataset identifying a plurality of patients, the initial dataset comprising prescription information indicating a plurality of adherence levels respectively by the plurality of patients to a plurality of medications prescribed in association with a respiratory condition; instructions for accessing an additional dataset identifying an additional plurality of patients, the additional dataset comprising prescription information indicating an additional plurality of adherence levels respectively by the additional plurality of patients to an additional plurality of medications prescribed in association with the respiratory condition; instructions for inputting the additional dataset into the machine learning model; and instructions for, after inputting the additional dataset into the machine learning model, outputting a result from the machine learning model, the result comprising a set of risk levels respectively associated with at least a portion of the additional plurality of patients.

BRIEF DESCRIPTION OF THE FIGURES

FIG. 1A depicts an overview of components and entities associated with the systems and methods, in accordance with some embodiments.

DETAILED DESCRIPTION

Figure 1B:
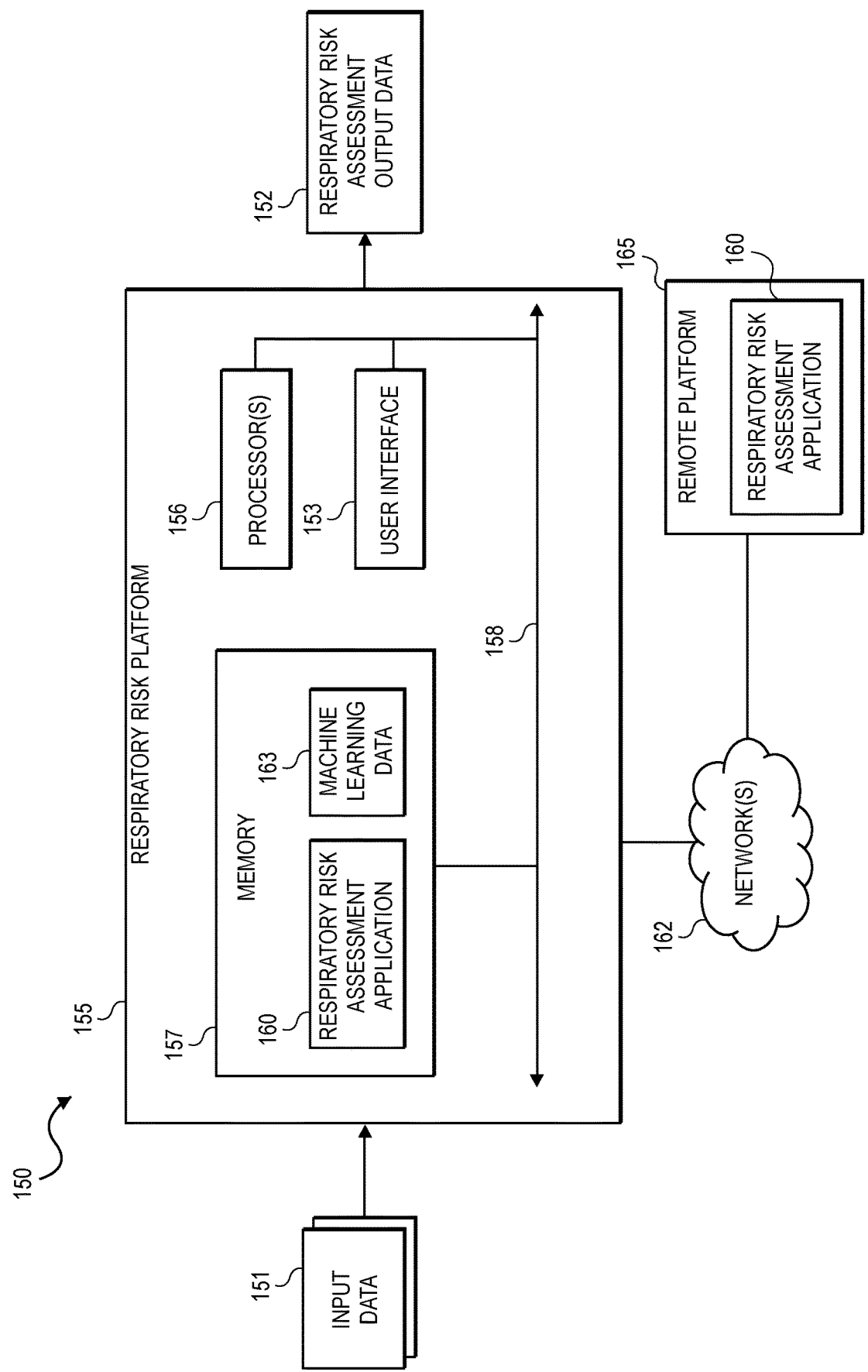
FIG. 1B depicts an overview of certain components configured to facilitate the systems and methods, in accordance with some embodiments.

The present embodiments may relate to, inter alia, platforms and technologies for using machine learning to predict risks posed to patients having respiratory conditions. According to certain aspects, a computing device may train a machine learning model using various medical and patient data, such as medication information, adherence levels, instances of additional care needed, patient attributes, and/or other information. The computing device may input, into the machine learning model, real-world data associated with a set of patients, and the machine learning model may output a respective set of likelihoods for the set of patients needing additional care for their respiratory conditions. Additionally, the computing device may facilitate an outreach to certain patients who are deemed to be at higher risk of needing additional care.

The systems and methods therefore offer numerous benefits. In particular, the use of various machine learning techniques enable the systems and methods to accurately, more consistently, and dynamically assess or predict risks that certain patients face in association with treatment of their respiratory conditions. This is particularly beneficial because medical personnel are able to undertake outreach efforts to advise patients on the importance of adhering to prescribed medications, thereby preempting the need for additional care in some cases. Thus, the systems and methods may lead to reduced instances of emergency room and urgent care visits and hospitalizations by patients, which increases the health of patients with respiratory conditions, decreases the strain on healthcare systems, and reduces the costs incurred by insured individuals and other people. It should be appreciated that additional benefits are envisioned.

The systems and methods discussed herein address a challenge that is particular to patient care. In particular, the challenge relates to a difficulty in accurately and effectively assessing whether and how a particular patient may be at risk for additional treatment, specifically related to respiratory conditions. In existing situations, a patient having a respiratory condition may suddenly and without warning need additional treatment. For example, a patient having asthma may experience an "asthma attack" and need care at an emergency room or urgent care facility. The systems and methods offer improved capabilities to solve these problems by using a trained machine learning model to accurately predict the likelihood that certain patients having respiratory conditions may need additional care. Further, because the systems and methods employ communication between and among multiple devices, the systems and methods are necessarily rooted in computer technology in order to overcome the noted shortcomings that specifically arise in the realm of patient care.

FIG. 1A illustrates an overview of a system 100 of components configured to facilitate the systems and methods. It should be appreciated that the system 100 is merely an example and that alternative or additional components are envisioned.

As illustrated in FIG. 1A, the system 100 may include a set of electronic devices 101, 102, 103. Each of the electronic devices 101, 102, 103 may be any type of electronic device such as a mobile device (e.g., a smartphone), desktop computer, notebook computer, tablet, phablet, GPS (Global Positioning System) or GPS-enabled device, smart watch, smart glasses, smart bracelet, wearable electronic, PDA (personal digital assistant), pager, computing device configured for wireless communication, and/or the like. In embodiments, any of the electronic devices 101, 102, 103 may be an electronic device associated with an individual (e.g., a patient) or an entity such as a company, business, corporation, or the like (e.g., a server computer or machine).

The electronic devices 101, 102, 103 may communicate with a server computer 115 via one or more networks 110. In embodiments, the network(s) 110 may support any type of data communication via any standard or technology (e.g., GSM, CDMA, VoIP, TDMA, WCDMA, LTE, EDGE, OFDM, GPRS, EV-DO, UWB, Internet, IEEE 802 including Ethernet, WiMAX, Wi-Fi, Bluetooth, and others). The server computer 115 may be associated with an entity such as a company, business, corporation, or the like. In some embodiments, the server computer 115 may be associated with medical care, such as a pharmacy, hospital, medical practice, physician, pharmaceutical company, or the like. The server computer 115 may include various components that support communication with the electronic devices 101, 102, 103.

The server computer 115 may communicate with one or more data sources 106 via the network(s) 110. In embodiments, the data source(s) 106 may compile, store, or otherwise access information associated the treatment of respiratory conditions. For example, the data source 106 may be IBM® MarketScan®. Additionally or alternatively, the data source(s) 106 may include data shared by health insurance payers via a data use agreement (e.g., emergency room and hospitalization data for asthma patients), pharmacy claims data that may be used to derive outcomes to influence a machine learning model (e.g., an increase in medication dose or a new drug therapy may indicate an escalation of the respiratory condition). It should be appreciated that alternative and additional data sources are envisioned.

Generally, the data source(s) 106 may store information indicating medications or combinations of medications that are prescribed to patients, instances of additional or intervention care (e.g., emergency room or urgent care visits, or hospitalizations) needed by patients, medication adherence information, and various patient attributes. For example, the information may indicate patients aged 18-39 with one or more COPD-specific maintenance medications as well as patients aged 40-64 with one or more COPD/asthma maintenance medications. Generally, some maintenance medication overlap exists between and asthma and COPD. Accordingly, patients aged 40-64 who have at least one COPD/asthma overlap medication may be included in the information. Because COPD in younger patients may still occur but is less common, patients aged 18-39 that require a COPD-specification medication may still be included in the information. This information may be embodied as a training dataset 116. In some implementations, the server computer 115 may access the training dataset 116 from one or more of the electronic devices 101, 102, 103.

The server computer 115 may receive or access the training dataset 116, and may employ various machine learning techniques, calculations, algorithms, and the like to generate a set of machine learning models using the training dataset 116. In particular, the server computer 115 may initially train a set of machine learning models using the training dataset 116 and then apply or input a validation set into a set of generated machine learning models to determine which of the machine learning models is most accurate or otherwise may be used as the final or selected machine learning model.

According to embodiments, the server computer 115 may input, into the generated machine learning model, a set of input data (which may be a set of real-world patient data) associated with a set of patients having a respiratory condition(s), a result of which may indicate a likelihood of each of the set of patients needing additional care stemming from the underlying respiratory condition. The server computer 115 may prioritize the respective likelihoods included in the output and generate outreach instructions associated with the higher-priority patients, and provide the outreach instructions to the electronic devices 101, 102, 103. A user of the electronic devices 101, 102, 103 (e.g., a pharmacist, nurse, physician, etc.) may review the outreach instructions and initiate communication with the indicated patients. In embodiments, a user may access the outreach instructions directly from the server computer 115. According to embodiments, the initiated communication may be an attempt to educate the patient on the importance of medicine adherence, to instruct the patient how to use certain medication, to answer any questions, or for other purposes.

The server computer 115 may be configured to interface with or support a memory or storage 113 capable of storing various data, such as in one or more databases or other forms of storage. According to embodiments, the storage 113 may store data or information associated with the machine learning models that are generated by the server computer 115. Additionally, the server computer 115 may access the data associated with the stored machine learning models to input a set of inputs into the machine learning models.

Although depicted as a single server computer 115 in FIG. 1A, it should be appreciated that the server computer 115 may be in the form of a distributed cluster of computers, servers, machines, or the like. In this implementation, the entity may utilize the distributed server computer(s) 115 as part of an on-demand cloud computing platform. Accordingly, when the electronic devices 101, 102, 103 interface with the server computer 115, the electronic devices 101, 102, 103 may actually interface with one or more of a number of distributed computers, servers, machines, or the like, to facilitate the described functionalities.

Although three (3) electronic devices 101, 102, 103, and one (1) server computer 115 are depicted in FIG. 1A, it should be appreciated that greater or fewer amounts are envisioned. For example, there may be multiple server computers, each one associated with a different entity. FIG. 1B depicts more specific components associated with the systems and methods.

FIG. 1B an example environment 150 in which a set of input data 151 is processed into respiratory risk assessment output data 152 via a respiratory risk platform 155, according to embodiments. In one implementation, the set of input data 151 may be a training dataset. The respiratory risk platform 155 may be implemented on any computing device, including the server computer 115 (or in some implementations, one or more of the electronic devices 101, 102, 103) as discussed with respect to FIG. 1A. Components of the computing device may include, but are not limited to, a processing unit (e.g., processor(s) 156), a system memory (e.g., memory 157), and a system bus 158 that couples various system components including the memory 157 to the processor(s) 156. The computing device may further include various communication components (e.g., transceivers and ports) that may facilitate data communication with one or more additional computing devices.

In some embodiments, the processor(s) 156 may include one or more parallel processing units capable of processing data in parallel with one another. The system bus 158 may be any of several types of bus structures including a memory bus or memory controller, a peripheral bus, or a local bus, and may use any suitable bus architecture. By way of example, and not limitation, such architectures include the Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

The respiratory risk platform 155 may further include a user interface 153 configured to present content (e.g., the content of the input data 151 and/or the output data 152, and information associated therewith). Additionally, a user may make selections to the content via the user interface 153, such as to navigate through different information, review certain input data, and/or other actions. The user interface 153 may be embodied as part of a touchscreen configured to sense touch interactions and gestures by the user. Although not shown, other system components communicatively coupled to the system bus 158 may include input devices such as cursor control device (e.g., a mouse, trackball, touch pad, etc.) and keyboard (not shown). A monitor or other type of display device may also be connected to the system bus 158 via an interface, such as a video interface. In addition to the monitor, computers may also include other peripheral output devices such as a printer, which may be connected through an output peripheral interface (not shown).

The memory 157 may include a variety of computer-readable media. Computer-readable media may be any available media that can be accessed by the computing device and may include both volatile and nonvolatile media, and both removable and non-removable media. By way of non-limiting example, computer-readable media may comprise computer storage media, which may include volatile and nonvolatile, removable and non-removable media implemented in any method or technology for storage of information such as computer-readable instructions, routines, applications (e.g., a respiratory risk assessment application 160), data structures, program modules or other data. Computer storage media may include, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by the processor 156 of the computing device.

The respiratory risk platform 155 may operate in a networked environment and communicate with one or more remote platforms, such as a remote platform 165, via a network(s) 162, such as a local area network (LAN), a wide area network (WAN), telecommunications network, or other suitable network. The remote platform 165 may be implemented on any computing device, including one or more of the electronic devices 101, 102, 103, or the server computer 115 as discussed with respect to FIG. 1A, and may include many or all of the elements described above with respect to the platform 155. In some embodiments, as will be described herein, the respiratory risk assessment application 160 as will be further described herein may be stored and executed by the remote platform 165 instead of by or in addition to the platform 155.

The respiratory risk assessment application 160 may employ machine learning techniques such as, for example, a regression analysis (e.g., a logistic regression, linear regression, or polynomial regression), k-nearest neighbors, decisions trees, random forests, boosting, neural networks, support vector machines, deep learning, reinforcement learning, Bayesian networks, or the like. When the data 151 is a training dataset, the respiratory risk assessment application 160 may analyze/process the data 151 to generate the machine learning model for storage as part of machine learning data 163 that may be stored in the memory 157.

When the data 151 comprises real-world patient data to be analyzed using the machine learning model, the respiratory risk assessment application 160 may analyze or process the data 151 using the machine learning model to generate an output that may comprise a set of values indicative of a set of risks posed to the patients included in the real-world patient data. In particular, the set of values may be indicative of a set of likelihoods that the patients may need additional care for respiratory conditions (e.g., emergency room or urgent care visits, or hospitalizations).

Generally, each of the data 151 and the data 152 may be embodied as any type of electronic document, file, template, etc., that may include various textual content and, for the data 152, a set of risks or likelihoods that a set of patients may need additional or intervention care for respiratory conditions, and may be stored in memory as program data in a hard disk drive, magnetic disk and/or optical disk drive in the respiratory risk platform 155 and/or the remote platform 165.

The respiratory risk assessment application 160 (or another component) may cause the respiratory risk assessment output data 152 (and, in some cases, the training or input data 151) to be displayed on the user interface 153 for review by the user of the respiratory risk platform 155. The user may select to review and/or modify the displayed data. For instance, the user may review the output data 152 to assess the risks that certain patients may face in association with respiratory conditions. Alternatively or additionally, the user may review contact or outreach information associated with the patients that may enable the user or the application 160 to contact certain patients that may face a higher risk of additional or intervention care.

In general, a computer program product in accordance with an embodiment may include a computer usable storage medium (e.g., standard random access memory (RAM), an optical disc, a universal serial bus (USB) drive, or the like) having computer-readable program code embodied therein, wherein the computer-readable program code may be adapted to be executed by the processor 156 (e.g., working in connection with an operating systems) to facilitate the functions as described herein. In this regard, the program code may be implemented in any desired language, and may be implemented as machine code, assembly code, byte code, interpretable source code or the like (e.g., via Golang, Python, Scala, C, C++, Java, Actionscript, Objective-C, Javascript, CSS, XML). In some embodiments, the computer program product may be part of a cloud network of resources.

Figure 2:
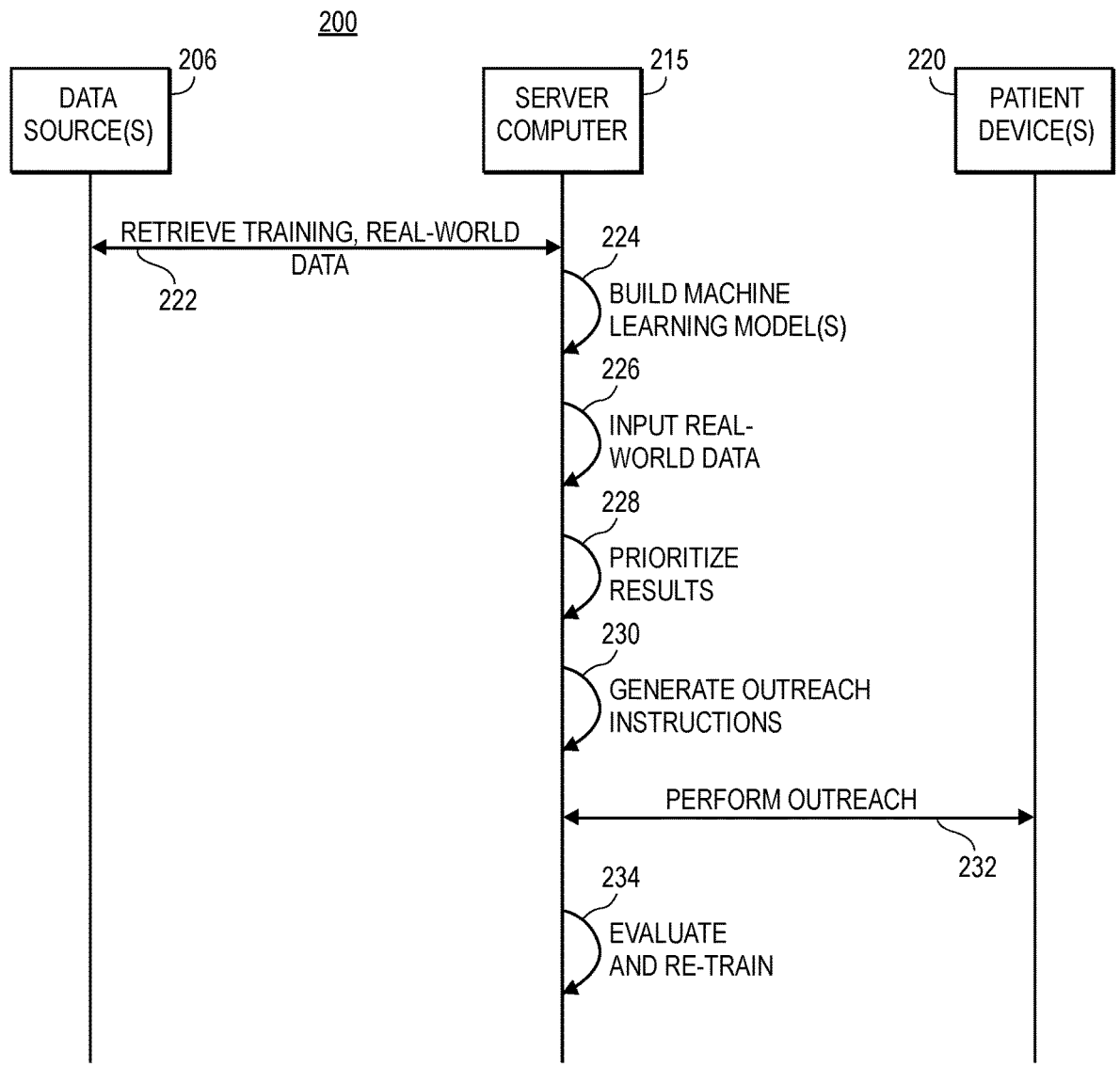
FIG. 2 depicts an illustration of an example signal diagram associated with generating and using a machine learning model to predict patient risk, in accordance with some embodiments.

FIG. 2 illustrates an example signal diagram 200 of certain components that may facilitate certain machine learning functionalities in association with assessing or predicting patient risk. The signal diagram 200 includes a data source(s) 206 (such as the data source(s) 106 as discussed with respect to FIG. 1A), a server computer 215 (such as the server computer 115 as discussed with respect to FIG. 1A), and a set of patient devices 220. It should be appreciated that alternative or additional components are envisioned.

As depicted in FIG. 2, the server computer 215 may retrieve (222), from the data source(s) 206 various sets of data, such as a set of training data and a set of real-world patient data, each of which may be a set of real-world data comprising information associated with medications prescribed to certain patients for the treatment of certain respiratory conditions. Each set of data may identify, for each patient, a medication or combination of medications that were prescribed to the patient. For example, the medications or medication combinations may include inhaled corticosteroids (ICS), a ICS/long-acting beta2-agonist combination (ICS-LABA), an oral therapy through leukotriene receptor antagonists (oral LRAs), an oral LRA plus ICS, an oral LRA plus ICS-LABA, an ICS plus ICS-LABA, an oral LAR plus ICS plus ICS-LABA, a rescue inhaler, and or other medications or medication combinations. Additionally, each set of data may indicate prescription refill information (i.e., when and how often a particular medication was refilled), and a proportion of days covered for each medication (e.g., based on a rolling 12-month calculation). Further, each set of data may indicate information or attributes associated with the patients such as, for example, gender, age, number of non-respiratory condition medications, a population density associated with an area in which the patient lives, and/or other information.

In some embodiments, the set of data may be specific to patients having asthma, COPD, or another respiratory condition. For example, for patients having COPD, the set of data may indicate medications or medication combinations (e.g., ICS-LABA, long-acting muscarinic receptor antagonists (LAMAs), ICS-LABA plus LAMAs), and an indication for each of the following: whether at least one prescription for a rescue inhaler was filled, whether at least one prescription for a Beta2-Adrenergic Agonist was filled, whether at least one prescription for a glucocorticosteroid was filled, whether at least one prescription for a diabetes medication was filled, and/or whether at least one prescription for a mental health medication was filled. Additionally, the set of data may indicate information or attributes associated with the patients such as, for example, a proportion of days covered for each maintenance medication, rescue inhaler, and Beta2-Adrenergic Agonist (e.g., based on a rolling 12-month calculation), a number of non-COPD medications, gender, and age.

According to embodiments, each set of data may be organized in a variety of ways. In particular, each set of data may be organized by the type of prescribed medication or combination of prescribed medications, and may indicate respective percentages of patients having the prescribed medication or combination of prescribed medications, respective percentages of the patients having a prescribed rescue inhaler, respective percentages of the patients having a prescribed rescue inhaler who had an emergency room or urgent care clinic visit, or hospitalization, and respective percentages of patients without a prescribed rescue inhaler who had an emergency room or urgent care clinic visit, or hospitalization.

Additionally or alternatively, each set of data may be organized by the medications themselves, and may indicate respective percentages of patients having the prescribed medication and having (or not having) a prescribed rescue inhaler, respective percentages of the patients having a prescribed rescue inhaler who had an emergency room or urgent care clinic visit, or hospitalization, and respective percentages of the patients without having a prescribed rescue inhaler who had an emergency room or urgent care clinic visit, or hospitalization.

Additionally or alternatively, each set of data may indicate adherence levels associated with the medication prescriptions. In particular, the set of data may indicate respective adherence levels of patients having particular prescribed medications who had an emergency room or urgent care clinic visit, or hospitalization, and respective adherence levels of patients having particular prescribed medications who did not have an emergency or urgent care visit, or hospitalization. According to embodiments, an adherence level may be any measure such as, for example, a proportion of days covered (PDC), medication possession ratio (MPR), or another measure, that may be calculated based on pharmacy data. An MPR is calculated as the ratio of the amount of days a patient has his/her medication on hand to the amount of days a patient is eligible to have the medication on hand, where the ratio is ideal or 100% or 1:1, and a PDC is calculated by the ratio of the number of days the patient is covered by the medication to the number of days the patient is eligible to have the medication on hand, and is capped at 100%. For example, the set of data may indicate the mean PDC for those patients having prescribed a rescue inhaler, with and without any emergency room, urgent care, or hospital visit.

Alternatively or additionally, each set of data may be organized using additional attributes. In particular, each set of data may indicate respective percentages of the patients who had (or did not have) an emergency room or urgent care clinic visit, or hospitalization, based on the following attributes: number of non-respiratory condition medications, age, gender (male or female), high population density (i.e., a population density that at least meets a threshold), and low population density (i.e., a population density that does not meet a threshold). Moreover, each set of data may be segmented or organized in other ways or according to other attributes. For example, a given set of data may include a first set of data for pediatric patients and a second set of data for adult patients.

The server computer 215 may build (224) a machine learning model(s) using one or more datasets retrieved from the data source(s) 26 or otherwise accessed. According to embodiments, the server computer 215 may divide or segment a set of data into a training set and a validation set, where there may or may not be overlap between the training set and the validation set. The server computer 215 may create, using the training set, a set of machine learning models. In embodiments, the server computer 215 may create any number of machine learning models of various types, for example a flat model, a hierarchical model, a network model, a relational model, an object-relational model, or other types of machine learning models.

The server computer 215 may apply or input the validation set into each of the created machine learning models. In applying or inputting the validation set into each of the created machine learning models, the server computer 215 may determine which of the machine learning models is most accurate or otherwise may be used as the final or selected machine learning model. In particular, the prediction may represent the selected machine learning model into which real-world data may be input, where the selected machine learning model may generate an output based on the trained and validated machine learning model.

As illustrated in FIG. 2, the server computer 215 may input (226) the real-world set of data into the machine learning model, where the real-world set of data may indicate a set of patients and characteristics of the patients. The machine learning model may output, for each patient of the set of patients, a risk score or other similar metric. In embodiments, the risk score may indicate a likelihood of that patient needing additional or intervention care, such as needing to visit the emergency room, urgent care, or hospital, in a subsequent amount of time (e.g., a month, six months, a year, etc.). The risk score may be a probability or other numeric indication, wherein the higher the risk score, the greater probability of that patient needing additional or intervention care (or vice-versa). For example, a particular patient who is 50 years old with asthma and who has a PDC of 0.60 may have a risk score of 35% (i.e., a 35% chance of needing additional care in the next six months); and another patient who is 18 years old with asthma and who has a PDC of 0.80 may have a risk score of 2% (i.e., a 2% chance of needing additional care in the next six months).

The server computer 215 may prioritize (228) results/outputs from the machine learning model. In particular, the server computer 215 may order or prioritize the outputted risk scores in descending order (or in another order), such that the highest-risk patients are prioritized or otherwise included at the top of a listing. Continuing with the example, the patient with the 35% risk may be prioritized higher than the patient with the 2% risk score.

The server computer may also generate (230) outreach instructions. According to embodiments, the outreach instructions may generally identify a certain amount of patients who are deemed to be at high risk of having a respiratory condition-related emergency room or urgent care visit, or hospitalization. The certain amount of patients may be a set amount or may be those patients having a risk score that at least meets a threshold value. For example, the outreach instructions may identify the ten (10) patients who have the highest risk of a respiratory condition-related emergency room or urgent care visit, or hospitalization. For further example, the outreach instructions may identify those patients who have a probability of experiencing a respiratory condition-related emergency room or urgent care visit, or hospitalization, of at least 10%. The outreach instructions may include several types of information for the patients such as, for example, name, address, phone number, email address, age, gender, and/or other information.

The server computer 215 may perform (232) or facilitate an outreach with the set of patient devices 220 using the outreach instructions generated in (230). It should be appreciated that the server computer 215 may perform the outreach using a variety of techniques. In one example, a pharmacist, physician, nurse, or other medical personnel may perform an outreach (e.g., via email, phone, or the like) to the identified patient(s) or his/her caregiver(s), via the set of patient device(s) 220. In association with the outreach, the medical personnel may provide counseling to the patient or his/her caregiver regarding medication adherence, inhalation technique, general management associated with the respiratory condition, and/or other information or guidance. Accordingly, the patient or his/her caregiver may be notified or aware of an importance of adhering to prescribed medications, and/or other information communicated by the medical personnel. As a result, the patient or his/her caregiver may undertake remedial measures to decrease the risk of needing an emergency room or urgent care visit, or hospitalization.

The server computer 215 may also evaluate results and re-train (234) the machine learning model. In particular, the server computer 215 may continuously evaluate results from the patient outreach efforts and compile such post-outreach results. For instance, the results may indicate which forms of patient outreach were or were not receptive or effective. Further, the results may indicate whether the patients who were contacted actually needed additional care (i.e., whether those patients ended up having an emergency room or urgent care visit, or hospitalization). It should be appreciated that the results may be accumulated and compiled over a certain period of time after the outreach efforts. Additionally, the server computer 215 may retrain the machine learning model with such post-outreach results and input additional real-world data into the retrained machine learning model, which may re-prioritize certain of the patients. Moreover, the server computer may gather and compile user experience feedback related to execution of the outreach program.

Figure 3:
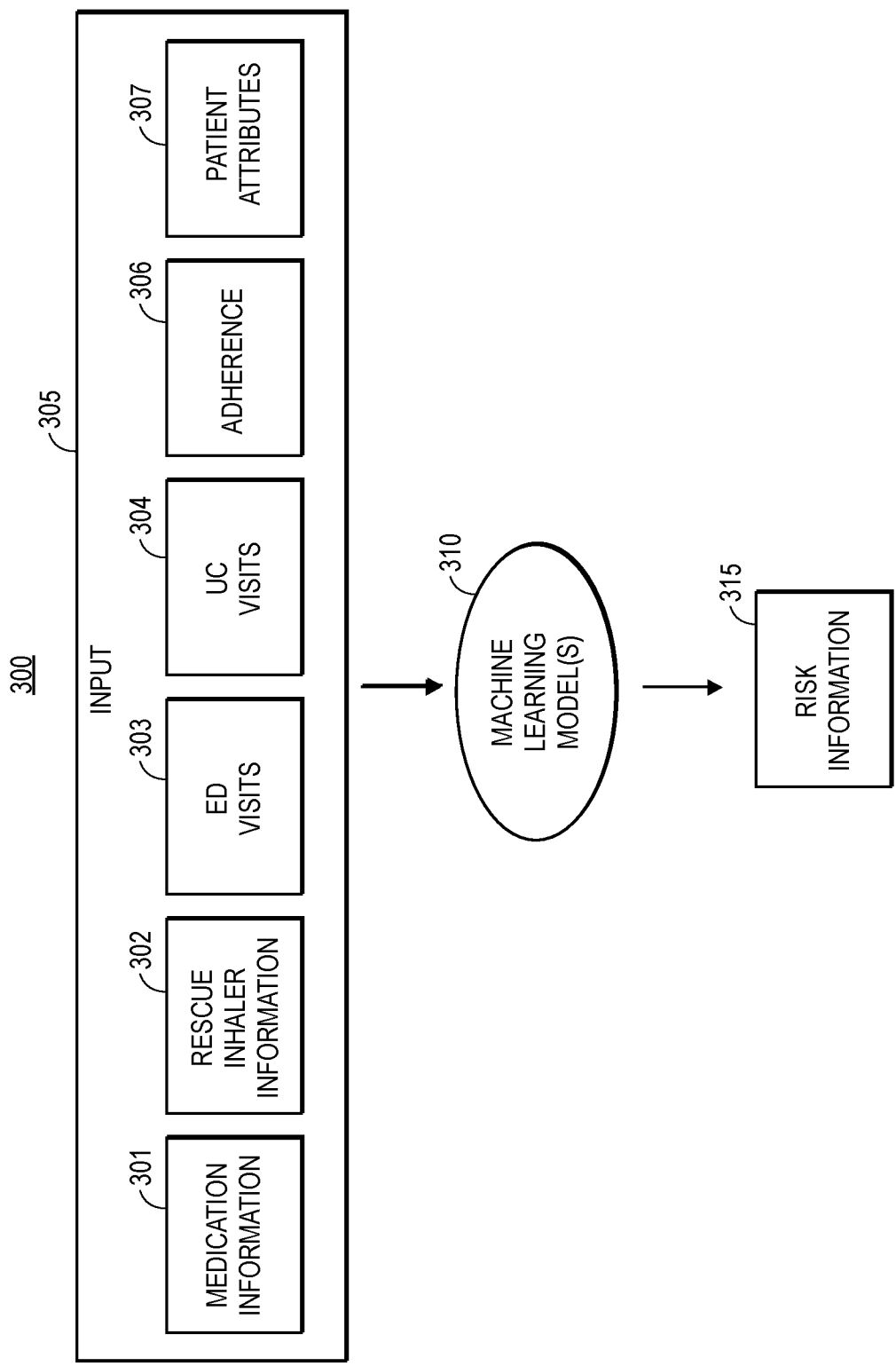
FIG. 3 depicts an example diagram including inputs and outputs associated with an example machine learning model, in accordance with some embodiments.

FIG. 3 illustrates a diagram 300 depicting inputs and outputs associated with a machine learning model. In particular, the diagram 300 includes a set of inputs 305 that represent parameters, information, attributes, and other data that may be used to initially train a machine learning model(s) 310, or otherwise be input into the machine learning model(s) 310. For example, as shown in FIG. 3, the set of inputs 305 may include medication information 301 that may identify medications or combinations of medications prescribed to a set of patients, rescue inhaler information 302 that may be a Boolean indicating whether a particular patient of the set of patients has prescribed a rescue inhaler, emergency department (ED) visit information 303 indicating which patients of the set of patients had an emergency room visit, urgent care (UC) or hospitalization visit information 304 indicating which patients of the set of patients had an urgent care visit or hospitalization, adherence information 306 indicting a measure of adherence that the set of patients have to prescribed medications, and patient attributes 307 including, for example, gender, age, number of non-respiratory condition medications, a population density associated with an area in which the patient lives, and/or other information.

In training the machine learning model(s) 310, a computing device may use the set of inputs 305 according to various techniques as discussed herein. Otherwise, when the machine learning model(s) 310 is trained, the computing device may input the set of inputs 305 into the machine learning model(s) 310, which may output a set of risk information 315. According to embodiments, the set of risk information 315 may indicate a risk level for at least a portion of the set of patients. For example, the risk level may be a calculated percentage chance that a given patient will need an emergency room, urgent care clinic, or hospital visit within a certain period of time (e.g., week, month, six months, year, etc.).

Figure 4:
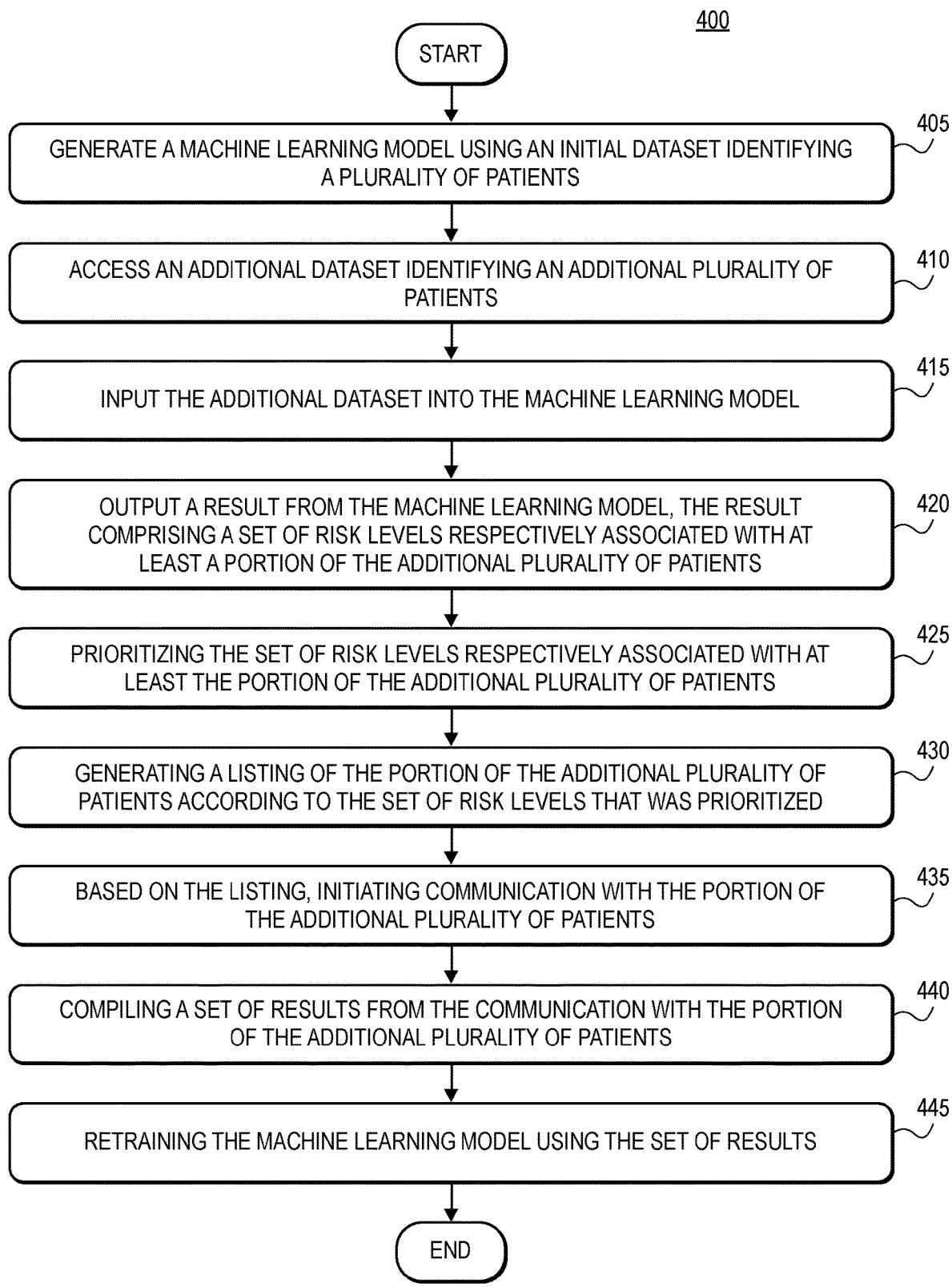
FIG. 4 is an example flowchart associated with predicting patient risk, in accordance with some embodiments.

FIG. 4 depicts is a block diagram of an example method 400 for predicting patient risk. The method 400 may be facilitated by an electronic device (such as the server computer 115 or components associated with the respiratory risk platform 155 as discussed with respect to FIGS. 1A and 1B) that may be in communication with additional devices or data sources.

The method 400 may begin when the electronic device generates (405) a machine learning model using an initial dataset identifying a plurality of patients. In embodiments, the initial dataset may include prescription information indicating a plurality of adherence levels respectively by the plurality of patients to a plurality of medications prescribed in association with a respiratory condition. Additionally, the initial dataset may further comprise data identifying the plurality of medications and, for each medication or combination of medications of the plurality of medications, a percentage of the plurality of patients who needed or had a visit to the emergency room, urgent care, or hospital. Further, the data identifying the plurality of medications may indicate, for each medication or combination of medications of the plurality of medications, a percentage of the plurality of patients who were prescribed a rescue inhaler.

Additionally, to generate the machine learning model, the electronic device may train the machine learning model using a training set comprising a first portion of the prescription information associated with a first portion of the plurality of patients, and validate the machine learning model using a validation set comprising a second portion of the prescription information associated with a second portion of the plurality of patients. In embodiments, the respiratory condition may be asthma, COPD, or another respiratory condition.

The electronic device may access (410) an additional dataset identifying an additional plurality of patients. According to embodiments, the additional dataset may include prescription information indicating an additional plurality of adherence levels respectively by the additional plurality of patients to an additional plurality of medications prescribed in association with the respiratory condition.

The electronic device may input (415) the additional dataset into the machine learning model. After inputting the additional dataset, the electronic device may output (420) a result from the machine learning model, where the result may include a set of risk levels respectfully associated with at least a portion of the additional plurality of patients.

The electronic device may prioritize (425) the set of risk levels respectively associated with at least the portion of the additional plurality of patients. The electronic device may further generate (430) a listing of the portion of the additional plurality of patients according to the set of risk levels that was prioritized. Further, the electronic device may, based on the listing, initiate (435) communication with the portion of the additional plurality of patients.

According to embodiments, the electronic device may compile (440) a set of results from the communication with the portion of the additional plurality of patients. In embodiments, the electronic device may access and compile the set of results over a time period after initiating the communication. Moreover, the electronic device may retrain (445) the machine learning model using the set of results.

Although the following text sets forth a detailed description of numerous different embodiments, it should be understood that the legal scope of the invention may be defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that may be permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that may be temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it may be communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment, or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also may include the plural unless it is obvious that it is meant otherwise.

This detailed description is to be construed as examples and does not describe every possible embodiment, as describing every possible embodiment would be impractical.

What is claimed is:

1. A computer-implemented method for predicting patient risk, the method comprising:

accessing, by a processor, a dataset identifying a plurality of patients, the dataset comprising (i) a first portion comprising first prescription information indicating a first plurality of adherence levels respectively by a first portion of the plurality of patients to a plurality of medications prescribed in association with a respiratory condition, where each patient in the first portion of the plurality of patients needed additional or intervention care, and (ii) a second portion comprising second prescription information indicating a second plurality of adherence levels respectively by a second portion of the plurality of patients to the plurality of medications prescribed in association with the respiratory condition, where each patient in the second portion of the plurality of patients did not need additional or intervention care;

training, by the processor, a machine learning model using the dataset comprising the first portion and the second portion;

accessing, by the processor, an additional dataset identifying an additional plurality of patients, the additional dataset comprising prescription information indicating an additional plurality of adherence levels respectively by the additional plurality of patients to an additional plurality of medications prescribed in association with the respiratory condition;

inputting, by the processor, the additional dataset into the machine learning model;

after inputting the additional dataset into the machine learning model, outputting, by the machine learning model, an output comprising a set of respective likelihoods of whether at least a portion of the additional plurality of patients will need additional or intervention care; and on a continuous basis:
  evaluating the output in combination with an outreach effort associated with at least the portion of the additional plurality of patients, and
  retraining, by the processor, the machine learning model based on evaluating the output in combination with the outreach effort.

2. The computer-implemented method of claim 1, wherein the respiratory condition is asthma or chronic obstructive pulmonary disease (COPD).

3. The computer-implemented method of claim 1, wherein the initial dataset further comprises data identifying the plurality of medications.

4. The computer-implemented method of claim 3, wherein the data identifying the plurality of medications indicates, for each medication or combination of medications of the plurality of medications, a percentage of the plurality of patients who were prescribed a rescue inhaler.

5. The computer-implemented method of claim 1, further comprising:
  prioritizing the set of respective likelihoods respectively associated with at least the portion of the additional plurality of patients; and
  generating a listing of the portion of the additional plurality of patients according to the set of respective likelihoods that was prioritized.

6. The computer-implemented method of claim 5, further comprising:
  based on the listing, initiating communication with the portion of the additional plurality of patients.

7. The computer-implemented method of claim 1, wherein the dataset further comprises a set of attributes associated with the plurality of patients.

8. A system for predicting patient risk, the system comprising:
  a processor;
  a memory storing data associated with a machine learning model; and
  a non-transitory computer-readable memory interfaced with the processor and the memory, and storing instructions thereon that, when executed by the processor, cause the processor to:
    access a dataset identifying a plurality of patients, the dataset comprising (i) a first portion comprising first prescription information indicating a plurality of adherence levels respectively by a first portion of the plurality of patients to a plurality of medications prescribed in association with a respiratory condition, where each patient in the first portion of the plurality of patients needed additional or intervention care, and (ii) a second portion comprising second prescription information indicating a second plurality of adherence levels respectively by a second portion of the plurality of patients to the plurality of medications prescribed in association with the respiratory condition, where each patient in the second portion of the plurality of patients did not need additional or intervention care,
    train the machine learning model using the dataset comprising the first portion and the second portion,
    access an additional dataset identifying an additional plurality of patients, the additional dataset comprising prescription information indicating an additional plurality of adherence levels respectively by the additional plurality of patients to an additional plurality of medications prescribed in association with the respiratory condition,
    input the additional dataset into the machine learning model,
    after inputting the additional dataset into the machine learning model, output, by the machine learning model, an output comprising a set of respective likelihoods of whether at least a portion of the additional plurality of patients will need additional or intervention care,
    on a continuous basis:
      evaluate the output in combination with an outreach effort associated with at least the portion of the additional plurality of patients, and
      retrain the machine learning model based on evaluating the output in combination with the outreach effort.

9. The system of claim 8, wherein the respiratory condition is asthma or chronic obstructive pulmonary disease (COPD).

10. The system of claim 8, wherein the dataset further comprises data identifying the plurality of medications.

11. The system of claim 10, wherein the data identifying the plurality of medications indicates, for each medication or combination of medications of the plurality of medications, a percentage of the plurality of patients who were prescribed a rescue inhaler.

12. The system of claim 8, wherein the processor is further configured to:
  prioritize the set of respective likelihoods respectively associated with at least the portion of the additional plurality of patients, and
  generate a listing of the portion of the additional plurality of patients according to the set of respective likelihoods that was prioritized.

13. The system of claim 12, wherein the processor is further configured to:
based on the listing, initiate communication with the portion of the additional plurality of patients.

14. The system of claim 8, wherein the dataset further comprises a set of attributes associated with the plurality of patients.

15. A non-transitory computer-readable storage medium having stored thereon a set of instructions, executable by a processor, for predicting patient risk, the instructions comprising:
instructions for accessing a dataset identifying a plurality of patients, the dataset comprising (i) a first portion comprising first prescription information indicating a plurality of adherence levels respectively by a first portion of the plurality of patients to a plurality of medications prescribed in association with a respiratory condition, where each patient in the first portion of the plurality of patients needed additional or intervention care, and (ii) a second portion comprising second prescription information indicating a second plurality of adherence levels respectively by a second portion of the plurality of patients to the plurality of medications prescribed in association with the respiratory condition, where each patient in the second portion of the plurality of patients did not need additional or intervention care;
instructions for training a machine learning model using the dataset comprising the first portion and the second portion;
instructions for accessing an additional dataset identifying an additional plurality of patients, the additional dataset comprising prescription information indicating an additional plurality of adherence levels respectively by the additional plurality of patients to an additional plurality of medications prescribed in association with the respiratory condition;
instructions for inputting the additional dataset into the machine learning model;
instructions for, after inputting the additional dataset into the machine learning model, outputting a result from the machine learning model, the result comprising a set of respective likelihoods of whether at least a portion of the additional plurality of patients will need additional or intervention care; and
instructions for, on a continuous basis:
evaluating the output in combination with an outreach effort associated with at least the portion of the additional plurality of patients, and
retraining the machine learning model based on evaluating the output in combination with the outreach effort.

16. The non-transitory computer-readable storage medium of claim 15, wherein the instructions further comprise:
instructions for prioritizing the set of respective likelihoods respectively associated with at least the portion of the additional plurality of patients; and
instructions for generating a listing of the portion of the additional plurality of patients according to the set of respective likelihoods that was prioritized.

* * * * *